United States Patent
Bouscarel et al.

(10) Patent No.: US 6,635,628 B2
(45) Date of Patent: Oct. 21, 2003

(54) METHODS OF ADMINISTERING CAMPTOTHECIN COMPOUNDS FOR THE TREATMENT OF CANCER WITH REDUCED SIDE EFFECTS

(75) Inventors: Bernard Bouscarel, Arlington, VA (US); Kunihiko Kobayashi, Urawa (JP)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 10/171,691

(22) Filed: Jun. 17, 2002

(65) Prior Publication Data

US 2002/0193391 A1 Dec. 19, 2002

Related U.S. Application Data

(62) Division of application No. 09/534,084, filed on Mar. 23, 2000, now Pat. No. 6,407,117, which is a continuation of application No. PCT/US99/13906, filed on Jun. 18, 1999.
(60) Provisional application No. 60/089,781, filed on Jun. 18, 1998.

(51) Int. Cl.[7] .................................. A61K 31/56
(52) U.S. Cl. ...................................................... 514/171
(58) Field of Search .......................................... 514/171

(56) References Cited

U.S. PATENT DOCUMENTS

| 5,225,404 A | 7/1993 | Giovannella et al. |
| 5,955,466 A | 9/1999 | Ulrich |

OTHER PUBLICATIONS

Takeda et al., International Journal of Cancer, 92 (2), pp269–75, (Apr. 15, 2001) Abstract Only.*
Dodds et al, J.Pharm. Scri., (1997), 86(12), 1410–1416 Abstract only.

* cited by examiner

Primary Examiner—Jerome D. Goldberg
(74) Attorney, Agent, or Firm—Antonelli, Terry, Stout, & Kraus, LLP

(57) ABSTRACT

Methods of administering camptothecin compounds such as irinotecan hydrochloride to reduce a diarrhea side effect and methods of treating cancer and AIDs with camptothecin compounds including administering the camptothecin compounds while maintaining the intestinal lumen and the bile at an alkaline pH.

1 Claim, 7 Drawing Sheets

METHODS OF ADMINISTERING CAMPTOTHECIN COMPOUNDS FOR THE TREATMENT OF CANCER WITH REDUCED SIDE EFFECTS

CROSS REFERENCE TO RELATED APPLICATIONS

This application is a Divisional Application of application Ser. No. 09/534,084, filed Mar. 23, 2000 now U.S. Pat No. 6,407,117, which is a continuation of PCT/US99/13906 filed Jun. 18, 1999 which claims the benefit of No. 60/089,781 filed Jun. 18, 1998.

FIELD OF THE INVENTION

The present invention relates to camptothecin compounds, in particular, irinotecan hydrochloride composition formulations, and methods of administering camptothecin compounds such as irinotecan hydrochloride for the treatment of cancer and AIDS, with reduced side effects.

BACKGROUND OF THE INVENTION

Camptothecin is a quinoline-based alkaloid found in the barks of the Chinese Camptotheca tree and the Asian nothapodytes tree. It is a close chemical relative to aminocamptothecin, CPT-11 (irinotecan), DX-8951F and topotecan. These compounds are useful in treating breast cancers, ovarian cancer, colon cancer, malignant melanoma, small cell lung cancer, thyroid cancers, lymphomas and leukemias. These compounds are also used for the treatment of AIDS.

Irinotecan hydrochloride (CPT-11) (4S)-4,11-diethyl-4-hydroxy-9-[(4-piperidinopiperidino)carbonyloxy]1H-pyrano [3',4':6,7] indolizino[1,2-b]quinoline-3,14(4 h, 12H) dione hydrochloride, has a novel mechanism of antitumor activity, namely the inhibition of DNA topoisomerase I. Topoisomer-ases are the enzymes which wind and unwind the DNA that makes up the chromosomes. As the chromosomes must be unwound to make proteins, camptothecin compounds keep the chromosomes wound tight so that they cannot make proteins. Because cancer cells grow at a much faster rate than normal cells, they are more vulnerable to topoisomerase inhibition than normal cells.

CPT-11 has shown effective antitumor activity clinically (2, 3), and, recently, a survival benefit by CPT-11 was shown in colorectal cancer. However, it has major toxicities of leukopenia and diarrhea in clinical practice. The clinical use of CPT-11 at higher dosages was associated with an unexpected and significant incidence of diarrhea (4, 6, 7, 12), and diarrhea is now recognized as a dose-limiting toxicity of this drug (4–7). Although many pharmacokinetic analyses, which have shown a great interpatient variability, have been made to predict the incidence of diarrhea, there are somewhat conflicting results (8–11).

CPT-11 and its metabolites, SN-38 and SN-38-Glu, were detected in not only human plasma but also human bile. Of the three compounds, SN-38 has strong cytotoxicity, SN-38-Glu is a deactivated, glucuronidated form of SN-38, and CPT-11 has much less cytotoxicity compared to SN-38. These compounds have an α-hydroxy-3-lactone ring, which undergoes reversible hydrolysis at a rate that depends mainly on pH (15, 16, 17). At more than physiological pH, the lactone form is unstable and the equilibrium favors hydrolysis to open the lactone ring and yield the carboxylate form. Under acidic conditions, the reverse reaction, with formation of the lactone, is favored. Similar reactions also occur with CPT-11 and SN-38-Glu.

From several reports, it is considered that major metabolic pathways in human are as follows; CPT-11 is hydrolyzed by carboxylesterase of mainly liver origin to the active metabolite, 7-ethyl-10-hydroxy-camptothecin (SN-38). Some of SN-38 undergoes subsequent conjugation by the hepatic enzyme, UDP-glucuronyltransferase, to SN-38 β-glucuronide (SN-38-Glu), and is excreted into bile along with the other components, CPT-11 and SN-38 (13, 14). The three compounds are believed to be reabsorbed by intestinal cells to enter the enterohepatic circulation. Recently, it has been found that hepatic cytochrome P-450 3A enzymes metabolize CPT-11 to 7-ethyl-10-[4-N-(5-aminopentanoic acid)-1-piperidino]carbonyloxycamptothecin, which has 500-fold weaker antitumor activity than SN-38 (Rivory et al., 1996b; Haaz et al., 1997). CPT-11, SN-38 and SN38-Glu have an α-hydroxy-3-lactone ring, which undergoes reversible hydrolysis at a rate which is mainly pH-dependent (Fassberg et al., 1992). At physiological pH and higher, the lactone form is unstable and the equilibrium favors hydrolysis to open the lactone ring and yield the carboxylate form. Under acidic conditions, lactone-carboxylate interconversion is shifted toward the lactone form. CPT-11, SN-38 and SN38-Glu are excreted into bile and along with it are released into the small intestinal lumen (Atsumi et al., 1991; Lokiec et al., 1995; Chu et al., 1997a, b). Furthermore, although minor (Atsumi et al 1995), an additional pathway involves direct transport of CPT-11 and its metabolites from serum to lumen across the intestinal epithelial cells. Once in the intestine, SN38-Glu can be deconjugated in the cecum and colon to SN-38 by bacterial β-glucuronidase (Takatsuna et al., 1996). CPT-11, SN-38 and SN38-Glu are believed to be reabsorbed to a certain extent by intestinal cells and to enter the enterohepatic circulation.

To date, there is little information about the intestinal uptake and transport mechanism of CPT-11 and its derivatives. This knowledge is a critical step in the understanding of the mechanism by which CPT-11 induces diarrhea. In the present study, the uptake of CPT-11 and SN-38 by intestinal epithelial cells was estimated and correlated to their respective effect on cell toxicity.

The structure of several camptothecin derivatives are known.

Glycosylated Analogs of 7-Hydroxymethylcamptothecin

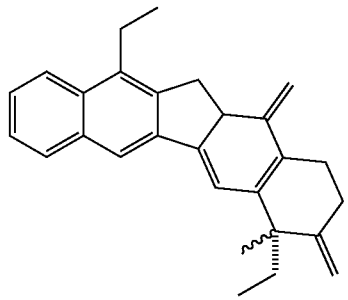

7-hydroxymethyl camptothecin
HAR8

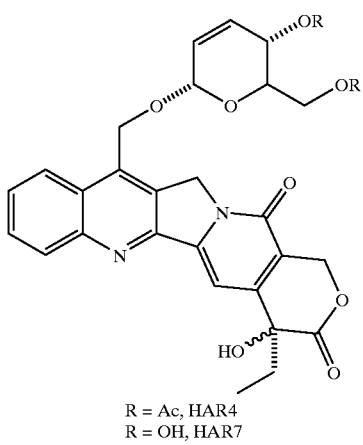

R = Ac, HAR4
R = OH, HAR7

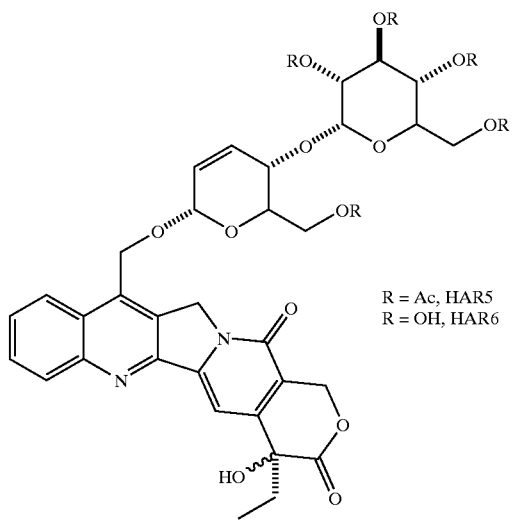

R = Ac, HAR5
R = OH, HAR6

Camptothecin and Analogs Currently in Clinical Development

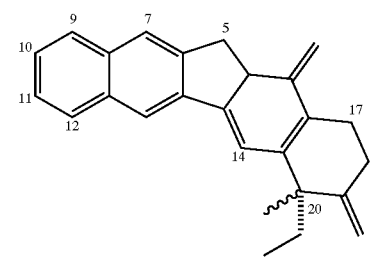

Camptothecin

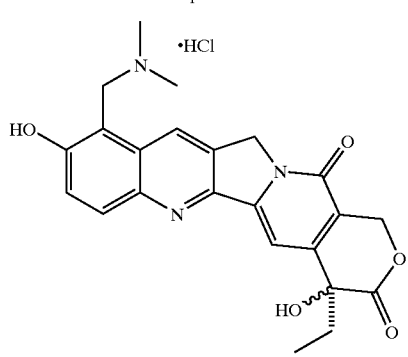

Topotecan

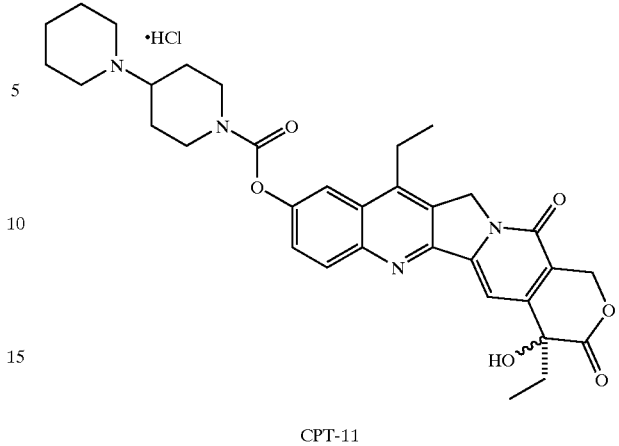

CPT-11

In addition, U.S. Pat. No. 5,552,154 discloses that camptothecin (CPT) and derivatives thereof of the closed lactone ring form are administered intramuscularly or orally. In such cases, it was possible to obtain total remissions of a vast spectrum of human cancers without the toxicity observed previously with CPT Na+. The derivatives of CPT used were 9-Amino-20 (S)-Camptothecin (9AC). 9-Nitro-20(S)-Camptothecin ($9NO_2$).

U.S. Pat. No. 5,468,754 describes that CPT 11 and other camptothecin derivatives undergo an alkaline, pH-dependent hydrolysis of the E-ring lactone. The slow reaction kinetics allow one to assess whether both lactone and non-lactone forms of the drug stabilize the topoisomerase-cleaved DNA complex. Studies indicate that only the closed lactone form of camptothecin helps stabilize the cleavable complex. Therefore, the patent recommends that pH levels of below 7 be used to allow the lactone form of camptothecin to predominate. The patent suggests the administration of the compounds with a pharmaceutically acceptable acid.

U.S. Pat. No. 5,447,936 describes that the HECPT form of the drug is more effective in inhibiting topoisomerase-I in an acidic environment, than in cells having higher intracellular pH levels. The patent describes the administration of the drug with an acid which is an organic carboxylic acid such as citric acid.

U.S. Pat. No. 5,225,404 describes the administration of a camptothecin compound with water-based solvents for water-soluble compounds such as normal saline or phosphate buffered saline solutions. The patent indicates that signs of diarrhea and cystitis were prevented and no overall toxicity was obtained.

U.S. Pat. No. 5,637,770 describes the creation of a hexacyclic compound obtained by the addition of a water-soluble ring to camptothecin, which had superior characteristics to camptothecin. U.S. Pat. No. 5,633,016 describes a combination cancer therapy including administering an effective amount of topotecan with cisplatin.

U.S. Pat. No. 5,633,260 discloses a 7–11-substituted camptothecin derivative. The patent also describes that maintaining an acidic pH (3 to 4) in the formulation is important to reduce the slow conversion of 11,7-HECPT lactones with the E-ring-hydrolyzed carboxylate which occurs at physiological pH. This patent prescribes regulated dosages to eliminate toxicity of the compound.

U.S. Pat. No. 5,652,244 describes a method of treating human carcinoma with camptothecin derivatives. U.S. Pat.

No. 5,658,920 describes a hexacyclic compound derivative of camptothecin.

U.S. Pat. No. 5,597,829 discloses that CPT is excreted unchanged by the kidneys, although a large percentage of the drug administered cannot be accounted for in the urine. The patent suggests that enhanced renal excretion of the carboxylate form of CPT occurs when exposed to a pH lower than 5. Therefore, it is recommended the administration of the drug to assure an acidic pH value by administering the compound with organic carboxylic acids.

U.S. Pat. No. 5,674,874 describes the pharmacologic conversion of CPT 11 to HECPT. The patent describes administration of the compound in sufficient quantities to maintain the pH of the formulation from about 2 to about 6 with the administration of a pharmaceutically acceptable acid.

Cancer Investigation, Volume 14, Supplement 1, No. 31, describes the use of irinotecan (CPT 11) to treat colon cancer and non-small cellular lung cancer. The publication confirms the incidence of grade 4 diarrhea associated with administration of CPT 11 dropped from 17% to 5% following adoption of an aggressive loperimide therapy.

Irinotecan Approved for Advance Colorectal Cancer, Med. Sci. Bull 1996; Volume 18, No. 12, describes that diarrhea is a common side effect of irinotecan administration.

Journal of the National Cancer Institute, Sep. 4, 1996, Vol. 88, No. 17, suggests that excessive production of sulphomucin in the cecum could be the major cause of CPT-11-induced diarrhea.

The Camptosar Patient Management Guidelines suggest avoiding the diarrhea side effect of camptosar by administering loperimides and gatorade.

The present invention overcomes one of the major side effects, diarrhea, associated with administration of camptothecin compounds, in particular irinotecan hydrochloride. This is one of the major deficiencies in the prior art in delivering irinotecan hydrochloride for the treatment of tumors. The present invention overcomes the diarrhea side effect associated with the administration of irinotecan hydrochloride and its related compounds.

SUMMARY OF THE INVENTION

The present invention provide for methods of administering camptothecin compounds which are cleared through the liver, preferably irinotecan hydrochloride and its derivatives.

The invention provides a method of inhibiting a diarrhea side effect of camptothecin compounds cleared by the liver, including but not limited to, irinotecan hydrochloride (CPT-11), SN38-Glu, and SN-38 comprising administering irinotecan hydrochloride while the intestinal lumen is maintained an alkaline pH.

The invention also provides a method of treating cancer comprising administering camptothecin compounds such as irinotecan hydrochloride while maintaining the intestinal lumen at an alkaline pH.

In a preferred embodiment the cancer is selected from, but not limited to, breast cancer, ovarian cancer, colon cancer, malignant melanoma, small cell lung cancer, thyroid cancers, lymphomas and leukemias.

In another embodiment the invention provides a method of treating AIDS comprising administering irinotecan hydrochloride while maintaining the intestinal lumen at an alkaline pH.

The invention advantageously provides a method of administering a camptothecin compound such as irinotecan hydrochloride (CPT-11) intravenously comprising prior to or simultaneously administering said camptothecin compound, orally administering a bicarbonate and alkaline $H_2O$.

The invention provides a method of administering a camptothecin compound such as irinotecan hydrochloride (CPT-11) intravenously comprising prior to or simultaneously administering said camptothecin compound, orally administering a composition comprising borbic acid.

The invention also provides for a method of administering a camptothecin compound comprising prior to or simultaneously administering said camptothecin compound, orally administering a composition comprising urso-deoxycholic acid.

Throughout the present specification where compositions, kits, and methods are described as including or comprising specific components, it is contemplated by the inventors that compositions of the present invention also consist essentially of or consist of the recited components.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

Figure 1:
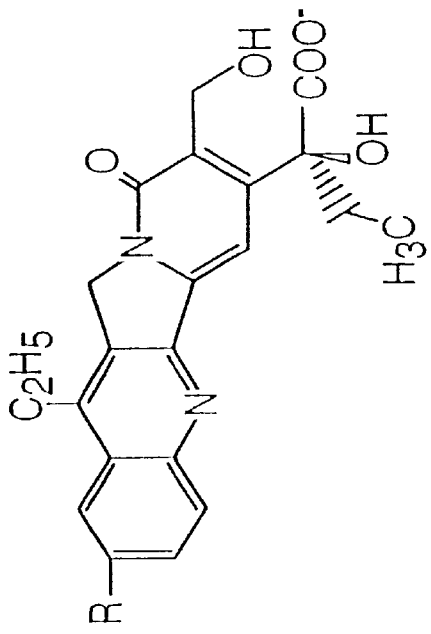
FIG. 1 shows structures of CPT-11, SN-38 and SN-38-glucuronide (SN-38-GLU): Lactone forms of CPT-11 and SN-38 are non-ion charged, and carboxylate forms of CPT-11 and SN-38 are anions. Not only carboxylate form of SN-38-Glu but also its lactone form, which possesses an additional carboxyl group in its glucuronide moiety, is an anion. The reversible conversion between lactone and carboxylate forms is pH driven.
Figure 1:
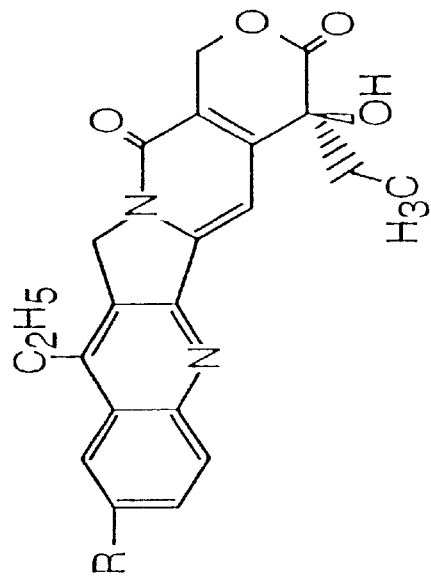
Figure 1:
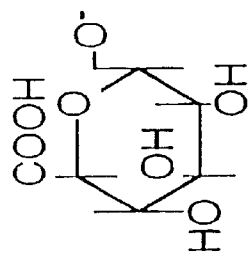
Figure 1:
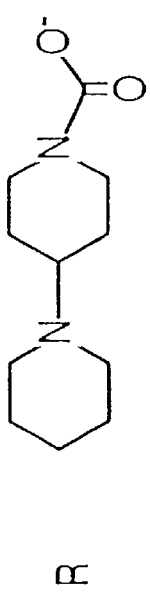

Knowledge of the cellular transport mechanism of camptothecin compounds such as CPT-11 and its metabolites by the intestine is a critical step in the understanding of the mechanism by which camptothecin compounds, such as CPT-11, induce diarrhea and its great interpatient variability in pharmacokinetics. The inventors reviewed the uptake of several camptothecin compounds, CPT-11 and SN-38, by intestinal epithelial cells. The results provide for the new design of an approach to prevent diarrhea and large interpatient variability in pharmacokinetics in clinical practice of the treatment of cancer and tumors with irinotecan hydrochloride and its related compounds.

The invention provides a method of inhibiting a diarrhea side effect of camptothecin compounds such as irinotecan hydrochloride (CPT-11), SN-38-Glu, SN-38 and its derivatives comprising administering irinotecan hydrochloride while maintaining the bile and/or intestinal lumen at an alkaline pH. In a preferred embodiment the intestinal lumen is maintained at an alkaline pH by administration of bicarbonate and alkaline H$_2$O. The amount of bicarbonate and alkaline pH is suitable to reduce the uptake of the camptothecin compound and thus reduce the cytotoxic side effects including a diarrhea side effect. The camptothecin compound or irinotecan hydrochloride may be administered intravenously, orally or intramuscularly. The method of the invention inhibits the reabsorption and decreases the lactone uptake of CPT-11 and SN-38 by the intestines and thus reduces the diarrhea side effect associated with camptothecin compounds such as irinotecan hydrochloride.

The invention also provides a method of treating cancer comprising administering irinotecan hydrochloride and its derivatives or mixtures thereof, while maintaining the intestinal lumen at an alkaline pH. In a preferred embodiment the cancer is selected from the group consisting of, but not limited to breast cancer, ovarian cancer, colon cancer, malignant melanoma, small cell lung cancer, thyroid cancers, lymphomas and leukemias. The alkaline pH may be a pH from about 7 to about 10. In an alternative embodiment the cancer is treated by administering a compound selected from 7-hydroxymethyl camptothecin, irinotecan hydrochloride, aminocamptothecin, DX-8951F, SN-38, HAR4, HAR5, HAR6, HAR7, HAR8 and topotecan, while maintaining the intestinal lumen at an alkaline pH.

The invention advantageously provides for a method of treating AIDS comprising administering irinotecan hydrochloride or its derivatives while maintaining the intestinal lumen at an alkaline pH.

A pharmaceutical composition and kit including irinotecan hydrochloride (CPT-11) administered in combination with a bicarbonate selected from sodium bicarbonate, magnesium bicarbonate and potassium bicarbonate. Alternatively irinotecan hydrochloride (CPT-11) may be administered in combination with a composition comprising borbic acid. This chemical has been used in buffers composition, such as the Britton-Robinson buffer and has a strong alkalinic buffering action.

The invention also provides for a method of administering a camptothecin compound comprising prior to or simultaneously administering said camptothecin compound, orally administering a composition comprising urso-deoxycholic acid. This composition may optionally be administered with bicarbonate. It is believed that urso-deoxycholic acid stimulates bicarbonate secretion into bile.

The following example shows the ability to reduce the diarrhea side effect of irinotecan hydrochloride compounds in accordance with the method of the invention.

EXAMPLE

Drugs and Animals $^{14}$C-Labeled SN-38 (3.68 MBg/mg) and $^{14}$C-Labeled CPT-11 (1.47 MBq/mg) were kindly donated by Daiichi Pharmaceutical Co., Ltd. Tokyo, Japan). Non-labeled CPT-11, SN-38, and SN-38-Glu were supplied by Yakult Honsha Co., Ltd. Tokyo, Japan). $^{14}$C-labeled SN-38 was dissolved in DMSO at a final concentration 2 µM because it was very hydrophobic and poorly soluble in water. DMSO at 2% was confirmed to have no effect on the initial uptake of labeled CPT-11 and SN-38. The other drugs were dissolved in distilled water. The lactone and carboxylate forms of $^{14}$C-labeled CPT-11 and SN-38 were produced by dissolving the compound overnight in 50 mM phosphate buffer at pH 6. or 9, respectively. DNP-SG was made from glutathione and CDNB (1-chloro-2,4-dinitro benzene) chemically. All other reagents were of analytical grade. Adult male Golden Syrian hamsters (6–8 weeks age), whose model presents a bile acid profile similar to that observed in human (28), were used.

Preparation of Intestinal Cells

Intestinal cells were isolated as previously described (28, 29). Briefly, male hamsters were anesthetized with sodium pentobarbital (Nembutol 70 mg/kg body weight). The entire intestine was removed. The intestinal lumen was washed with 37° C. Hank's solution. Sacs of the ileum (12.5 cm from cecum) and jejunum (remaining small intestine) were rinsed, as well as the intestinal sacs of the anal site of small intestine (12.5 cm from cecum) and oral site (the other small intestine). The sacs were rinsed with oxygenated buffer solution containing sodium citrate (96 mM NaCl, 1.5 mM KCl, 5.6 mM $KH_2PO_4$, 27 mM sodium citrate, pH 7.3), and incubated for 10 min in the same buffer at 37° C. The sacs were then emptied, filled with oxygenated buffer solution containing EDTA (140 mM NaCl, 16 mM $Na_2HPO_4$, 2 mM EDTA, 0.5 mM dithiothreitol, pH 7.3), incubated for 10 min at 37° C. Then each sac was placed onto a petri dish and gently vortexed for 1 min. The buffer containing intestinal cells was recovered in 50 mL of Hanks' solution, washed twice and adjusted at $10^6$ cells/ml in Hanks' medium (cellular stock solution containing 0.5% bovine serum albumin, pH 7.4).

Determination of the Cellular Uptake of $^{14}$C-labeled CPT-11 and SN-38, Respectively Uptake of $^{14}$C-labeled CPT-11 and SN-38 was measured by rapid vacuum filtration assay (28, 29). The cellular suspension of 0.95 ml was incubated for 15 min in a 37° C. water bath with stirring. Uptake was started by the addition of 0.05 ml PBS (at pH 3 or 9) containing labeled SN-38 or CPT-11 at 37° C. At various time intervals, 100 μL, sample aliquots were diluted into 3 mL of Hank's medium at 4° C. to stop the uptake. The stop solution containing the cells was filtered through a glass microfiber filter (Glass Fiber Filter Circles G4, Fisherbrand, Pa.) under vacuum (20 psi). The cells were washed once with 5 mL of 0.5% bovine serum albumin-containing Hanks' medium (4° C.) and once with 20 mL of Hanks' solution (4° C.). The filters were placed in a vial containing 4 mL of scintillation liquid (Ultra Gold, Packard, Conn.) and the radioactivity was counted in a β scintillation counter (LS3801, Beckman, Md.).

The effect of the metabolic inhibitor, 2,4 dinitrophenol (1 mM), was studied by adding this agent to the cells 3 min prior to either $^{14}$C-CPT-11 or $^{14}$C-SN-38 (2 μM). The effect of 20 mM of taurocholic acid (TCA) on the uptake of both CPT-11 and SN-38 was investigated following overnight incubation of $^{14}$C-CPT-11 (20 μM) and $^{14}$C-SN-38 (2 μM) in Hank's solution, at pH 7.4 and in the presence and absence of TCA. The effect of 200 μM of DNP-SG or SN-38-Glu was also studied by adding these agents to the cell preparation 7 min prior to either $^{14}$C-CPT-11 (20 μM) and $^{14}$C-SN-38 (2 μM).

The effect of physiologic pH on the initial intestinal uptake rate of CPT-11 and SN-38 was investigated following overnight incubation of $^{14}$C-CPT-11 (20 μM) and $^{14}$C-SN-38 (2 μM) in phosphate buffered saline at pH 6.2, 6.8, 7.4 and 8, respectively.

Estimation of Micelle Formation

To assess whether or not CPT-11 and SN-38 form micelles, these agents were incubated overnight at pH 4 and 9 in a calcium and magnesium free Hank's solution containing 10 mM TCA. The respective solution was filtered through a 1000-molecular weight cut-off membrane YM1 (Diaflo, Amicon, Mass.) at a steady speed of 0.04 ml/min. Once the filtration was stopped, the radioactivity in the initial solution as well as in the filtrate and in the retained solution after filtration was determined as described previously.

Cytotoxicity Assay

Rapid colorimetric assay for mitochondrial dehydrogenase activity was modified and used for the estimation of cytotoxicity of SN-38 (Mosmann, 1983). Briefly, HT29 cells were seeded into a 12-well plate (Falcon-3043, Lincoln Park, N.J.), and, after 48 h, SN-38 (0.4 μM) at pH 6.2, 6.8, 7.4 and 8.0 was added. After 24 h-exposure, the cells were washed twice, and subjected to a drug-free incubation for 24 h. Then, the cells were incubated with 0.5 mg/ml 3-(4,5-dimethylthiazol-2-yl)-2,5-diphenyl-tetrazolium bromide (MTT) for 4 h, and the blue formazan crystals were solubilized by addition of 10% n-dodecylsulfate sodium salt (SDS) in 0.1N HCl and overnight incubation. The formation of the blue formazan compound is spectrophotometrically determined at 560 nm (Ultraspec 4050, LKB, Bromma, Sweden).

Statistical Analysis

The initial rate of uptake of CPT-11 or SN-38 was derived from the linear regression analysis of the respective regression line obtained from the plot of the uptake as a function of time. The initial rates of uptake were plotted against the corresponding concentration. The data were fitted by least-squares nonlinear regression analysis (SigmaStat, Jandel Scientific, CA), using the equation $V=(V_{max} \cdot S)/(K_m+S)+K_d \cdot S$ where V represents the initial rate of uptake. $V_{max}$ is the maximum rate of uptake, $K_m$ is the apparent Michaelis constant, $K_d$ is the rate of diffusion and S is the concentration of CPT-11 or SN-38.

Comparisons between two groups were evaluated by the Mann-Whitney Rank Sum Test. Statistical significance of differences among more than two groups was determined by Kruskal-Wallis One Way Analysis of Variance on Ranks, then multiple comparisons versus control group were performed by Dunn's Method. The correlation between the initial rate of uptake and the cytotoxicity of SN-38 was plotted by a simple least-squares regression method.

Figure 2A:
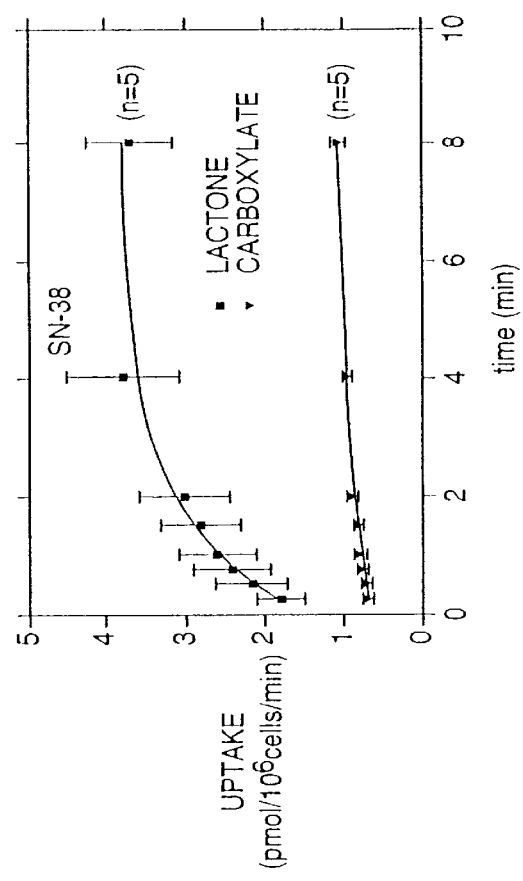
FIGS. 2A and 2B show the time course of CPT-11 and Sn-38 uptake by isolated intestinal cells: The uptake of $[^{14}C]$ CPT-11 (20 $\mu M$) and $[^{14}C]$ SN-38 (2 $\mu M$) in lactone and carboxylate form, respectively, by isolated intestinal cells from jejunum was measured as a function of time. At time 0, the respective agent was added to the intestinal cell suspension maintained at 37° C. under permanent shaking. At 15, 30, 45, 60, 90, 120, 240 and 480 sec, aliquots of cell suspension were removed, and processed as described in Materials and Methods. The results shown are mean±SE of n experiments.
Figure 2B:
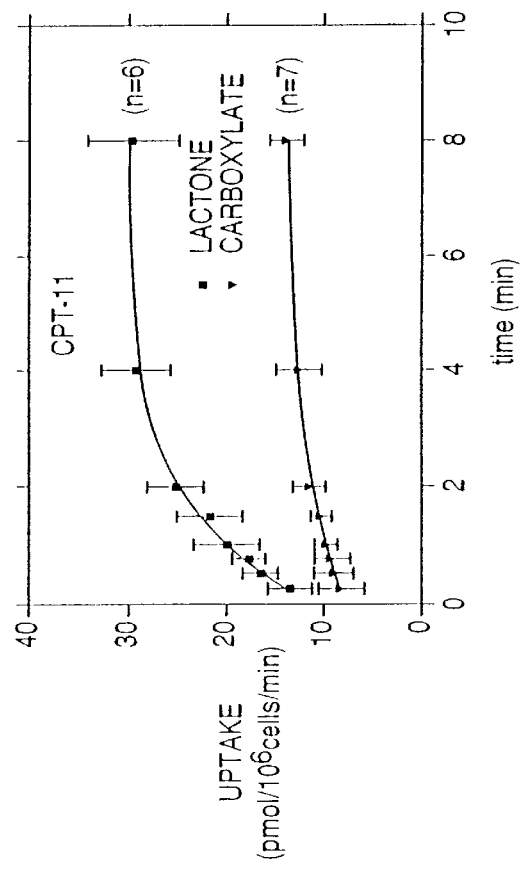
Figure 3A:
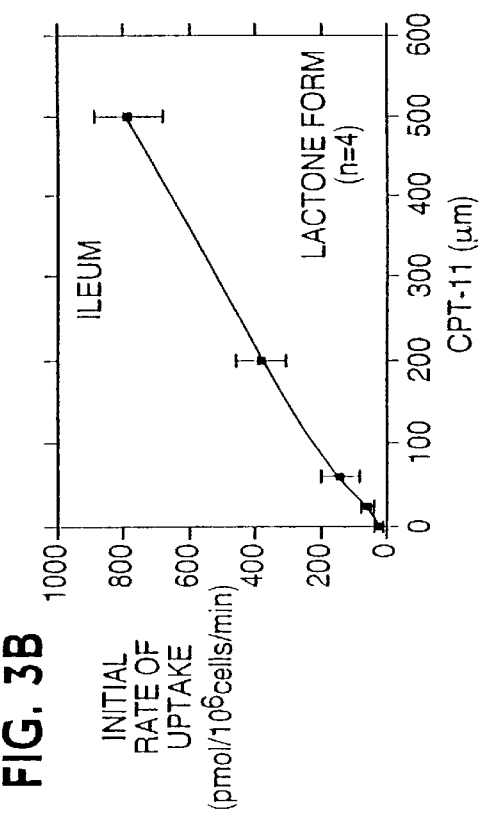
FIGS. 3A, 3B, 3C and 3D show the relationship between initial rate of uptake of CPT-11 and its concentration: The initial uptake rate was determined from the linear slope of the cellular uptake over the initial 90 sec incubation period. The data were fitted by least-square nonlinear regression analysis using the equation $V=(V_{max} S)/(K_m+S)+K_d S$ where V represents the initial rate of uptake, $V_{max}$ is the maximum rate of uptake, $K_m$ is the apparent Michaelis constant, $K_d$ is the rate of diffusion and S is the concentration of CPT-11.
Figure 3B:
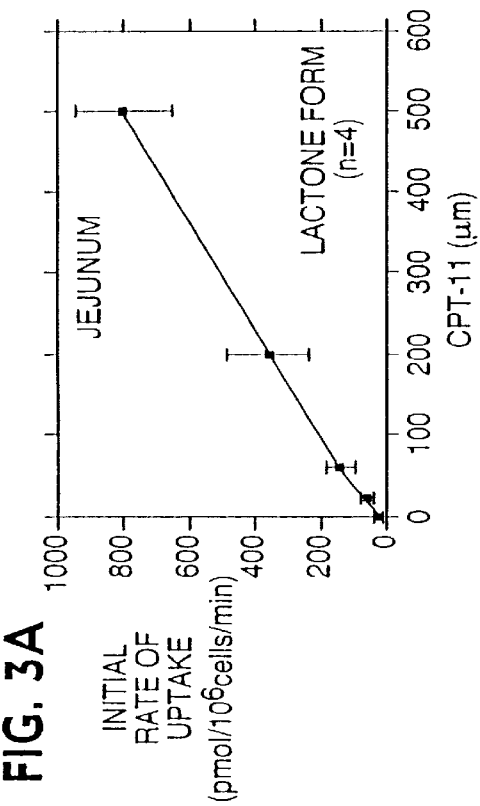
Figure 3C:
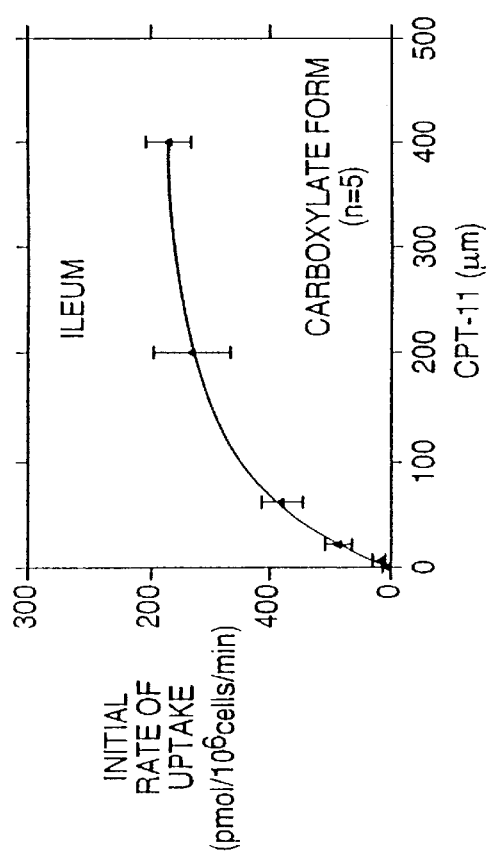
Figure 3D:
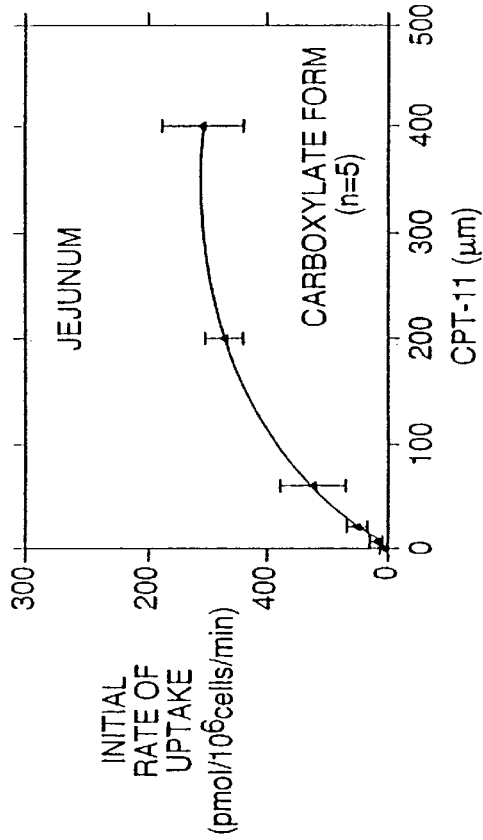

Uptake of CPT-11 and SN-38 Lactone and Carboxylate, Respectively by Intestinal Cells The time-dependent uptake of 20 μM $^{14}$C-CPT-11 and 2 μM $^{14}$C-SN-38 in both lactone and carboxylate forms by isolated jejunal cells is shown in FIG. 2. The extrapolation of the uptake value at time 0 yields a positive intercept, indicative of non-specific binding, such as adsorption to labeled agents on the cell surface. The respective uptake of the lactone and carboxylate forms of both CPT-11 and SN-38 was linear for up to 90 sec. Therefore, the initial uptake rate was determined by linear regression fit of the uptake over the initial period of time. Comparison of the uptake rate between the lactone and carboxylate form of the respective agent clearly showed a more rapid uptake of both CPT-11 and SN-38 lactone, as compared to carboxylate form (FIG. 2).

Table 1 summarizes the respective initial uptake rate of 20 μM $^{14}$C-CPT-11 and 2 μM $^{14}$C-SN-38 by jejunal and ileal cells. CPT-11 and SN-38 lactone were more rapidly taken up than their carboxylate forms in cells from both intestinal regions but without significant differences between jejunal and ileal cells.

Transport System of CPT-11 and SN-38 Lactone and Carboxylate

The respective initial uptake rate of CPT-11 lactone and carboxylate was plotted as a function of the concentration and the data for were fitted by least-squares nonlinear regression analysis using the equation $V=(V_{max} \cdot S)/(K_m+S)+K_d \cdot S$ (FIG. 3) in both jejunal and ileal cells, the predominant component of the uptake of CPT-11 lactone was non-saturable, suggesting uptake by either passive diffusion or fluid-phase endocytosis. The analysis of the curve of the uptake of CPT-11 carboxylate suggested also at least two separate components of the uptake process. The saturable component of the curve was characterized by a maximum rate of uptake ($V_{max}$) of 147 and 157 pmol·$10^6$ cell$^{-1}$·min$^{-1}$·$\mu$M$^{-1}$ and a Michaelis constant ($K_m$) of 51.3 and 50.5 $\mu$M in jejunal and ileal cells, respectively. The minor non-saturable component was characterized by a diffusion constant ($K_d$)<0.05 pmol·$10^6$ cell$^{-1}$·min$^{-1}$·$\mu$M$^{-1}$ and represented less than one twentieth of that for CPT-11 lactone in cells of both intestinal regions (Table 2). Furthermore, the Kd for CPT-11 lactone was 1.8–2.5 fold lower than that of SN-38 lactone.

Figure 4A:
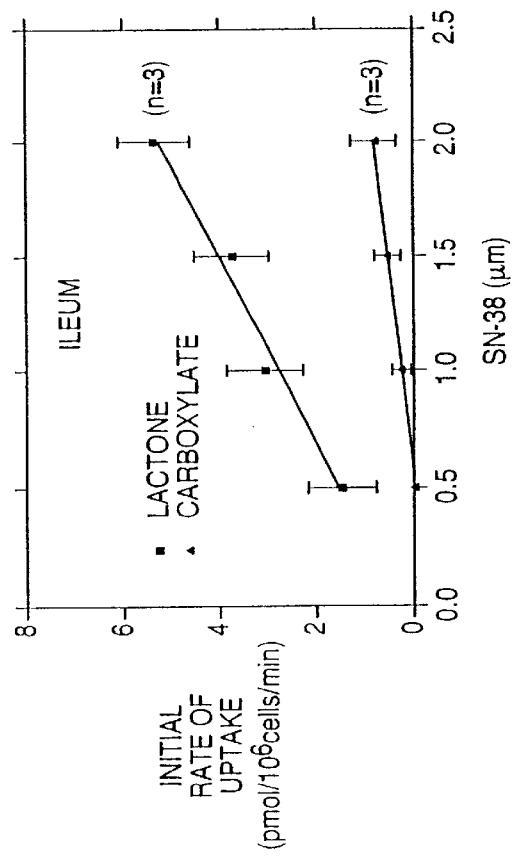
FIGS. 4A and 4B show the relationship between initial rate of uptake of SN-38 and its concentration. The initial uptake rate was determined as described in legend of FIG. 3 and in Materials and Methods. The data were fitted by least-square linear regression. Because of limited solubility, only concentrations of SN-38 up to 2 $\mu M$ were investigated.
Figure 4B:
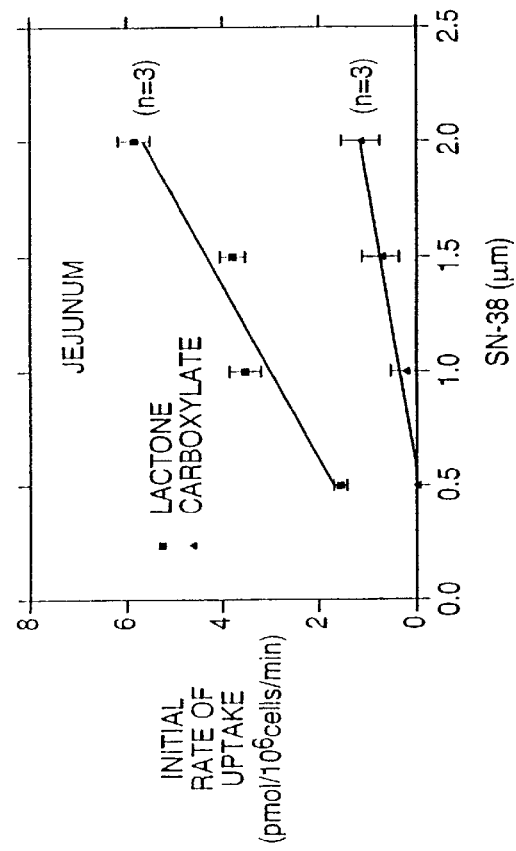

The initial uptake rate of SN-38 lactone and carboxylate was plotted as a function of the concentration (FIG. 4). The maximum concentration of SN-38 used in this study was lower than 2 $\mu$M due to the poor solubility of the compound and therefore rendered the determination of the saturable and unsaturable component of the uptake difficult. In this range of concentrations, the uptake of SN-38 lactone and carboxylate was mostly non-saturable (FIG. 4).

The carrier-mediated transport is known to be inhibited by metabolic poisons, such as 2,4-dinitrophenol, which interferes with cell metabolism and reduces energy-producing reactions (23). Therefore, 2,4-dinitrophenol was used in applicants study to determine the mechanism of uptake of CPT-11 and SN-38 lactone and carboxylate, respectively. The results of this study are summarized in Table 3. Although, the uptake rate of both CPT-11 and SN-38 lactone was not significantly affected by the addition of 2,4-dinitrophenol, the uptake rate of CPT-11 and SN-38 carboxylate was reduced to 22.6 and 30.8%, respectively by 2,4-dinitrophenol, suggesting an active transport mechanism for both of these compounds.

2,4-dinitrophenol-S-glutathione (DNP-SG) is known to be a substrate for the active multispecific organic anion transporter (cMOAT) in the liver (24). In addition, the conjugation by UDP-glucuronyltransferase of SN-38 leads to the formation of SN-38-Glu which is also a substrate for the hepatic cMOAT (12,17). To determine whether either CPT-11 carboxylate and/or SN-38 carboxylate is transported through a cMOAT-like mechanism in intestinal cells, the uptake rate of CPT-11 and SN-38 was studied in the presence or absence of both DNP-SG and SN-38-Glu. The results are summarized in Table 3. DNP-SG and SN-38-Glu significantly inhibited the the uptake of the carboxylate form of SN-38 by over 60% while that of CPT-11 carboxylate remained unchanged. The uptake rates of the lactone forms of CPT-11 and SN-38 were not significantly affected by the presence of either DNP-SG or SN38-Glu.

Micelle Formation and its Effect on the Initial Uptake Rate of CPT-11 and SN-38

Figure 5:
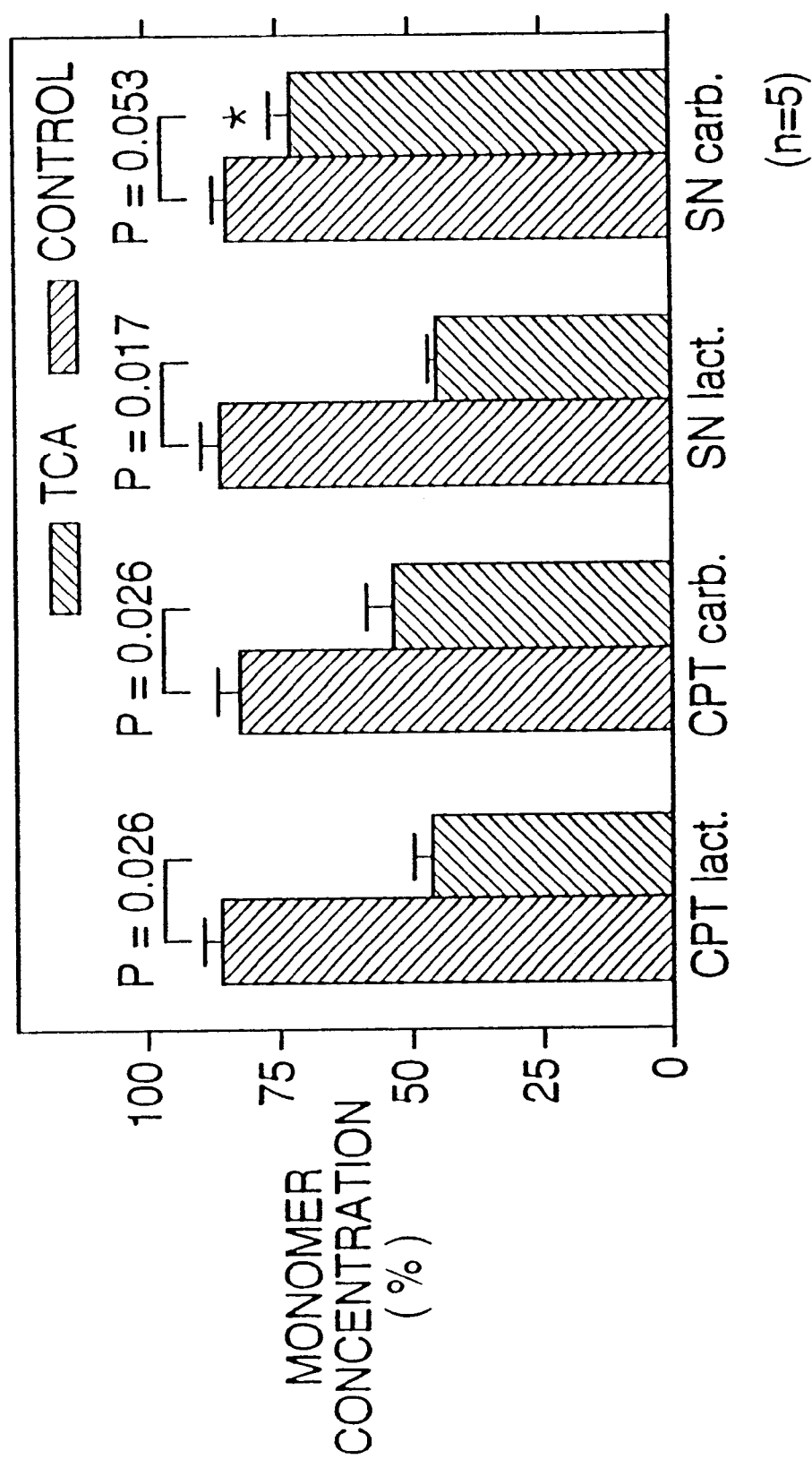
FIG. 5 shows the effect of taurocholate (TCA) on respective CPT-11 and SN-38 micelle formation: [$^{14}$C] CPT-11 (20 µM) and [$^{14}$C] SN-38 (2 µM) were stored overnight in Hank's solution in the presence of absence of TCA (20 mM). Monomers were separated from micellar aggregates by ultrafiltration through a 1000-molecular weight cut-off membrane (YM1) as described in Materials and Methods. Values are the monomeric forms of the indicated metabolites, expressed as a percentage (%) of the concentration of the initial solution before ultrafiltration. Comparison between TCA and control was estimated by Mann-Whitney test. ($^+$): Sn-38 carboxylate is significantly different from the other agents tested in the presence of TCA (Kruskal-Wallis test: p=0.023, Student-Newman-Keuls method, p<0.05). Abbreviations used: CPT lactone (CPT lact.); CPT carboxylate (CPT carb.); SN-38 lactone (SN lact.); and SN-38 carboxylate (SN carb.).

Taurocholic acid (TCA) at a concentration greater than its critical micellar concentration forms micelles (25) which in contrast to both CPT-11 and SN-38, cannot pass through a 1,000-molecular weight cut-off membrane. We used this property to determine whether or not CPT-11 and SN-38 lactone and carboxylate can associate to the TCA micelles. The results reported in FIG. 5, show that TCA significantly decreased the % monomer concentration of CPT-11 lactone and carboxylate as well as SN-38 lactone. However, SN-38 carboxylate did not significantly associate to TCA micelles.

Next applicants tested the effect of micelle formation on the cellular uptake of CPT-11 and SN-38. In this series of experiments, the cells from the jejunum and ileum were combined. In the presence of 20 mM TCA, the initial uptake rate (mean±SD) of CPT-11 and SN-38 was reduced to 48.5±10.8 and 69.3±12.7% of control without TCA, respectively (n=5, Mann-Whitney test, p=0.015 and p=0.343 for CPT-11 and SN-38, respectively).

Effect of pH and Bicarbonate on the Initial Uptake Rate of CPT-11 and SN-38

Figure 6A:
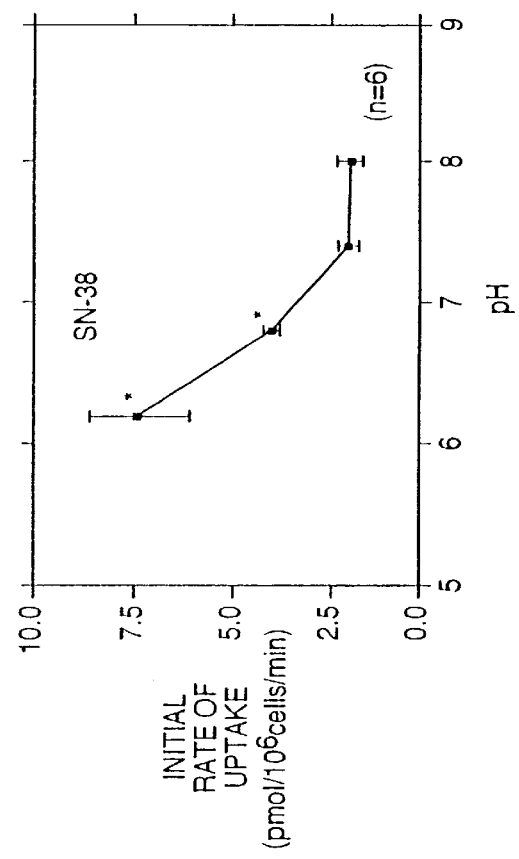
FIGS. 6A and 6B show the effect of pH on the initial rate of uptake of CPT-11 and SN-38: [$^{14}$C] CPT-11 (20 µM) and [$^{14}$C] SN-38 (2 µM) were dissolved in PBS at pH 6.2, 6.8, 7.4 and 8.0 and stored overnight. By adding the drugs to Hank's solution containing intestinal cells from whole small-intestine, uptake studies were performed. The difference in the initial uptake rate by pH was analyzed by Kruskal-Wallis test (p<0.001 and p<0.001 for CPT-11 and SN-38, respectively) and Student-Newman-Keuls method (*p<0.05).
Figure 6B:
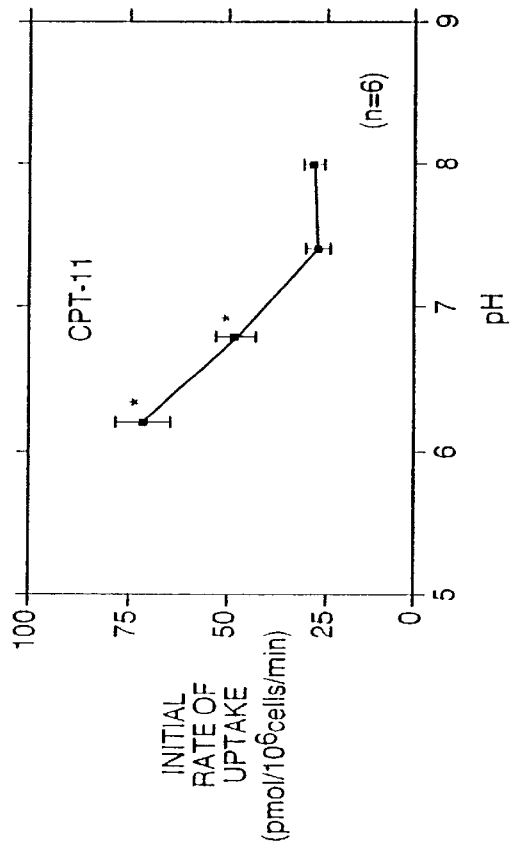

The interconversion between the lactone and carboxylate CPT-11 and SN-38, respectively, is reversible and pH-driven (11). The effect of physiological pH (pH 6.2 to 8) on the initial uptake rate of 20 $\mu$M $^{14}$C-CPT-11 and 2 $\mu$M $^{14}$C-SN-38 was studied. The results summarized in FIG. 6, show that the uptake rate of CPT-11 and SN-38 significantly decreased by around 65% at a pH greater than 6.8. Alteration of the uptake was also observed when the initial uptake rate of CPT-11 and SN-38 was measured in the presence and absence of bicarbonate. The uptake of CPT-11 and SN-38 was decreased when the HEPES component of the Hank's buffer was replaced by sodium bicarbonate and the pH adjusted to greater than 7.

Using hamster intestinal cells, the results of the present study show that the non-ionic, lactone forms of both CPT-11 and SN-38 were absorbed mainly through a passive mechanism but at a respective rate which was several times greater than their anionic carboxylate forms (Tables 1, 2 and 3; FIGS. 2, 3 and 4). There were significant differences in the transport mechanism as well as in the kinetic parameters between jejunal and ileal cells (Tables 2 and 3). Although not shown, similar results were also observed when the uptake of CPT-11 and SN-38 was performed using both cecal and colonic cells (26).

Figure 7:
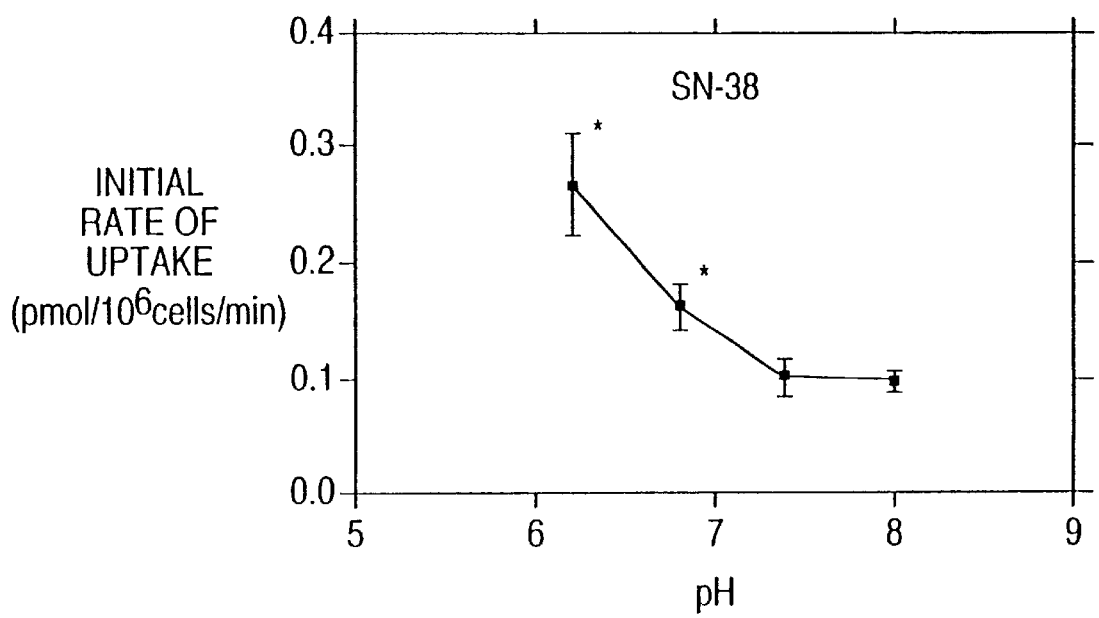
FIG. 7 shows the effect of pH on the initial uptake rate of HT29 cells. [$^{14}$C]SN-38 (2 µM) were dissolved in PBS at pH 6.2, 6.8, 7.4 and 8.0 overnight. The uptake study was initiated by adding the compounds to Hanks' solution containing HT29 cells. The comparative initial rate of uptake as function of pH was analyzed by Kruskal-Wallis test (p<0.001) and Dunn's method (*p<0.05).

Isolated hamster intestinal cells are not the best model to estimate the cytotoxic effect of SN-38 due to their limited viability to around 2 hours (Gore et al., 1993). Therefore, HT29 cells were also used to study the comparative effects of physiological pH on both the initial uptake rate of 2 $\mu$M [$^{14}$C]SN-38 and the cytotoxicity of 0.4 $\mu$M SN-38. The initial rate of uptake of SN-38 was lower in HT-29 cells than in isolated hamster intestinal cells.(FIGS. 3 and 4). However, as observed in isolated hamster intestinal cells, the uptake rate of SN-38 in HT29 cells was significantly greater at pH 6.2 and 6.8, than at pH 7.4 and 8.0 (Kruskal-Wallis test:P=0.008, Dunn's method:p<0.05) (FIG. 7). The cytotoxicity of SN-38 for HT29 cells was significantly higher at pH 6.2 and 6.8 than at pH 7.4 and 8.0 (Kruskal-Wallis test:P=0.007; Dunn's method:p<0.05). FIG. 5 shows the relationship between the initial rate of uptake of [$^{14}$C]SN-38 and the cytotoxicity of SN-38, indicating that, with decreasing pH, a higher uptake rate correlated with a more cytotoxic effect.

The results clearly showed that CPT-11 and SN-38 carboxylate were taken up by the intestinal cells through an active mechanism (Tables 2 and 3; FIG. 3). Recently, it has been proposed that cMOAT mostly expressed in hepatic canalicular membranes transports several types of organic anions into the bile as a primary active transport system (24, 27–29). Furthermore, the hepatic cMOAT has been reported to be responsible for the biliary excretion of the anions, SN-38 carboxylate, SN-38-Glu lactone and carboxylate (12, 17). The anion CPT-11 carboxylate was reported to be only partially eliminated through cMOAT (12, 17). The inventor's work shows that, in contrast to that of CPT-11 carboxylate, the initial uptake rate of SN-38 carboxylate was significantly inhibited by DNP-SG and SN-38-Glu (Table 3). These results are in accordance with those of Cho, et al (12, 17) using hepatic canalicular membrane vesicles. Therefore, this work underlines the involvement of a cMOAT or cMOAT-like transporter in jejunal and ileal cellular uptake of SN-38.

The inventors also reports that CPT-11 lactone and carboxylate, as well as SN-38 lactone can form micelles in the presence of high concentrations of TCA (FIG. 5). The percentage of the monomer concentration ranged from 38 to 47%. These concentrations differed from those of long-chain fatty acids (i.e. 2.3% for oleic acid) and from cholesterol (3%). Furthermore, micelle formation inhibited CPT-11 uptake, differing from the positive role bile acid micelle formation plays in the intestinal uptake of long-chain fatty acid and cholesterol. These results support data showing that micelle formation inhibited the uptake of short-chain fatty acids, such as palmitic acid.

As described in FIG. 1, the conversion from CPT-11 and SN-38 lactone to carboxylate is pH-driven (11, 12). It has previously been reported that at pH 7.4, 13% of SN-38 and CPT-11, respectively, were in their lactone form (30). The present study showed that the initial uptake rate of CPT-11 and Sn-38 was several times greater at acidic pH (pH 6.2 and 6.8) than that at neutral or alkaline pH (pH 7.4 and 8) (FIG. 6). Considering the fact that 1) at acidic pH, the non-ionic lactone form of CPT-11 and SN-38 are transported passively, 2) at neutral/basic pH, the anionic carboxylate form of CPT-11 and SN-38 are mostly absorbed actively, and 3) the uptake rates of both CPT-11 and Sn-38 lactone are several times greater than that of their carboxylate form, the mechanism of uptake of CPT-11 and SN-38 by intestinal cells closely resembles that of short-chain fatty acids. This hypothesis will be supported by the fact that, as with short-chain fatty acids, micelle formation reduced the uptake of CPT-11 and SN-38 and that the uptake of CPT-11 and SN-38 is not limited to the small intestine but also takes place in the cecum and colon.

Therefore, as for short-chain fatty acids, alkalinization of bile and luminal content reduce the intestinal uptake of CPT-11 and SN-38. The biliary content of CPT-11 and its metabolites was determined for two men who were treated by cisplatin and received CPT-11 intravenously (9). The major component of the bile was CPT-11 (75.6–91.9%) while SN-38 and SN-38-Glu were minor components, 0.9–3.3% and 7.3–18.9%, respectively. Furthermore, the pH of human bile has been reported to range from 6.5 to 8.0 (31). It is therefore, considered that not only the carboxylate but also lactone the form of CPT-11 plays an important role in pharmacokinetics due to the greater absorption of CPT-11 lactone by intestinal epithelial cells, resulting in an increased level of CPT-11 in the enterohepatic circulation.

SN-38 is active mainly as the lactone form, while SN-38 carboxylate exhibits only minor topoisomerase I-inhibitory activity (32). Using rat whole body autoradiography, 24 h after IV injection of $^{14}$C-SN-38, the radioactivity was found exclusively in the gastrointestinal tract (33). SN-38 exhibits strong cytotoxicity, SN38-Glu is a deactivated glucuronidated form of SN-38, and CPT-11 is much less cytotoxic compared to SN-38 (Kawato et al., 1991). Accumulation of SN-38 in the intestine was shown in rats (Atsumi et al., 1995), and was thought to be responsible for the diarrhea attributed to CPT-11 administration in nude mice (Araki et al., 1993). Disruption of the intestinal epithelium in the cecum was observed in mice and rats with diarrhea after CPT-11 administration (Takatsuna et al., 1996; Ikuno et al., 1995; Araki et al., 1993). The diarrhea induced by CPT-11 administration in human was reported to be secretory diarrhea (Bleiberg and Cvitkovic, 1996). However, as reported in the animal models, we observed lethal small-intestinal injury associated to CPT-11-induced side effects in patients (Kobayashi et al., 1998b).

Furthermore, accumulation of SN-38, the radioactivity was found exclusively in the gastrointestinal tract (33). Accumulation of SN-38 in the intestine was shown to be responsible for the diarrhea attributed to CPT-11 in nude mice (34). Disruption of the intestinal epithelium in the cecum was thought to be responsible for CPT-11-induced diarrhea in rat (35). Finally, from clinical estimations in Europe, the diarrhea induced by CPT-1 was reported to be secretory diarrhea (36), while in our study applicants experienced severe incidence of small-intestinal injury (37).

Autopsy revealed the presence of pseudomembranes jejunoileitis, of which the appearance under light microscopy was characterized by the disruption of the intestinal epithelium, suggesting that damage diarrhea could occur in severe cases. A mechanism for CPT-11-induced diarrhea is believed to include the reabsorption of mainly lactone SN-38 and CPT-11, by the intestinal epithelium, resulting in a high exposure of the intestinal epithelium to these metabolites which causes structural and functional injuries to the intestinal tract.

As suggested in the present study, alkalization of bile and/or intestinal luminal content reduces the uptake of and the exposure of the intestinal epithelium to CPT-11 and SN-38 lactone. The absorption of short-chain fatty acids in the intestine has been studied for the past decade, and there have been reports of conflicting results. It is believed that decreasing pH induces an increased uptake of short-chain fatty acids, as reported in FIG. 6. Thus, a prevention treatment of camptothecin and CPT-11-induced diarrhea focuses on two objectives: 1) alkalinization of the intestinal lumen, and 2) clearance of CPT-11 and SN-38 from the body (i.e. stool control). A combination of sodium bicarbonate, magnesium oxide and water at pH greater than 7 is administered orally to patients prior and/or simultaneously with standard IV administration of CPT-11. The incidence of diarrhea is decreased.

Figure 8:
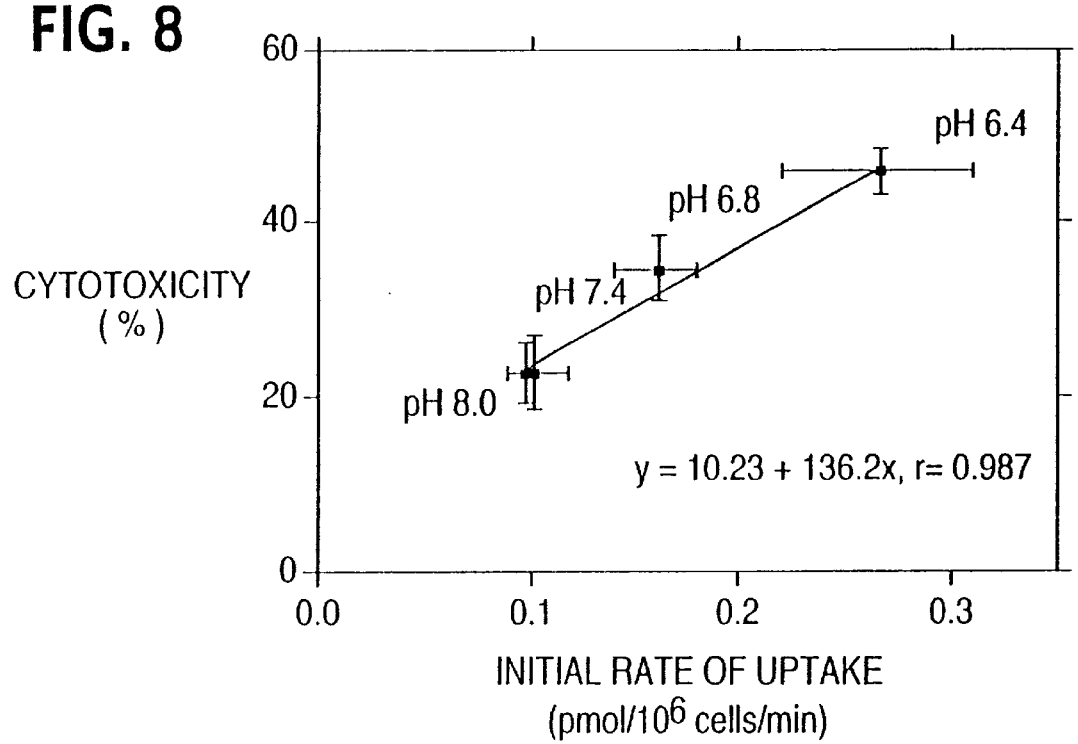
FIG. 8 shows the relationship between the initial uptake rate and the cytotoxicity of SN-38. Using HT29 cells, the effect of physiological pH on the initial uptake rate of 2 µM [$^{14}$C]SN-38 was estimated as described in legend of FIG. 3. The 0.4 µM SN-38-induced cytotoxicity in HT29 cells was studied by the described MTT assay. The relationship between the initial rate of uptake and the cytotoxicity of SN-38 was plotted by a simple least-squares regression method.

The relationship between the cellular uptake of SN-38 and its associated cytotoxicity was also estimated in the present study. It was found that the cellular uptake and cytotoxicity of SN-38 in HT29 cells was pH-dependent, and that the cytotoxicity correlated well with the initial uptake rate (FIG. 8). As previously described, it is considered that at acidic pH, the predominant form of SN-38 is lactone. This would lead to both a greater cellular uptake and intracelluar concentration of SN-38 lactone. Since SN-38 is active mainly as the lactone form, while SN-38 carboxylate exhibits only minor topoisomerase I-inhibitory activity (Kawato et al., 1991), this should be associated to an increased cell death. Therefore, one possible mechanism for CPT-11-induced diarrhea might include the reabsorption of SN-38 lactone by the intestinal epithelium, resulting in structural and functional injuries to the intestinal tract.

In summary, the present study is the first to estimate the uptake of CPT-11 and SN-38 by intestinal epithelial cells. CPT-11 and SN-38 lactone are both passively transported, while both CPT-11 and SN-38 carboxylate are actively absorbed. The uptake rate of CPT-11 and SN-38 lactone is several times greater than that of the respective carboxylate form. Furthermore, the higher uptake rate of SN-38 is associated with an increased cytotoxic effect in HT29 cells. These findings suggest that the converstion to carboxylate would reduce the cellular uptake of both CPT-11 and SN-38. Consequently, these findings provide support for alkalization of the intestinal lumen as a possible mechanism to reduce reabsorption of CPT-11 and SN-38 in clinical practice. It is possible that limited intestinal reabsorption in turn modulates the bioavailability of this drug circulating enterohepatically, and reduces the toxic side effects of SN-38 on intestinal epithelium.

The results directly impact clinical practice, and administration of camptothecin compounds which are cleared through the liver, such as irinotecan hydrochloride and its derivatives. The inventors provide for oral alkalinization with the administration of camptothecin compounds which are cleared through the liver, including CPT-11.

In conclusion, the inventors describe the uptake of camptothecin compounds such as CPT-11 and SN-38 by intestinal epithelium. CPT-11 and SN-38 lactone are both passively transported by intestinal cells. Both CPT-11 and SN-38 carboxylate are actively absorbed, although through different transport mechanisms. The formation of micelles with TCA reduced the uptake of both CPT-11 and SN-38. The uptake rate of CPT-11 and SN-38 lactone is several times greater than that of the carboxylate form while the uptake rate decreased in the presence of bicarbonate and under condition of increased pH. These findings for CPT-11 and SN-38 can be useful in clinical practice.

TABLE I

Initial rates of uptake of CPT-11 and SN-38 by intestinal cells.

| | jejunum | | ileum | |
|---|---|---|---|---|
| CPT-11 | | | | |
| Lactone | 85.6 ± 8.6 | $P < 0.001$ | 80.9 ± 10.6 | $P = 0.001$ |
| Carboxylate | 31.1 ± 3.8 | | 31.1 ± 4.2 | |
| SN-38 | | | | |
| Lactone | 6.76 ± 1.08 | $P = 0.004$ | 6.14 ± 1.02 | $P < 0.001$ |
| Carboxylate | 1.70 ± 0.27 | | 1.51 ± 0.20 | |

The initial rates of uptake of [$^{14}$C]CPT-11 (20 $\mu$M) and [$^{14}$C]SN-38 (2 $\mu$M), lactone and carboxylate, respectively, were compared. The results are expressed as p mol·10$^6$ cells$^{-1}$·min$^{-1}$ and are the mean±SE of 10 experiments. Mann Whitney test was used for statistical analyses.

TABLE II

Kinetic parameters of CPT-11 and SN-38 uptake by intestinal cells

| | jejunum | | | ileum | | |
|---|---|---|---|---|---|---|
| | Km | Vmax | Kd | Km | Vmax | Kd |
| CPT-11 | | | | | | |
| Lactone | ND | ND | 0.95 | ND | ND | 1.06 |
| | | | (0.15) | | | (0.28) |
| Carboxylate | 51.3 | 146.9 | <0.05 | 50.5 | 157.3 | <0.05 |
| | (16.3) | (41.3) | (<0.02) | (13.0) | (38.0) | (<0.02) |
| SN-38 | | | | | | |
| Lactone* | ND | ND | 2.38 | ND | ND | 1.87 |
| | | | (0.26) | | | (0.10) |
| Carboxylate* | ND | ND | 0.44 | ND | ND | 0.42 |
| | | | (0.17) | | | (0.01) |

(*): Because of limited solubility, only concentrations of SN-38 up to 2 $\mu$M were investigated.

(+): Because SN-38 carboxylate is judged to be actively transported from the estimation of its uptake in the presence of dinitrophenol (Table 3.), these values are not considered to be physiologically relevant.

NOTE:

The data were fitted by least-square nonlinear regression analysis using the equation V = (V$_{max}$ · S)/(K$_m$ + S) + K$_d$ · S. V$_{max}$ (p mol · 10$^6$ cells$^{-1}$ · min$^{-1}$) is the maximum rate of uptake, K$_m$ ($\mu$M) is the apparent Michaelis constant, K$_d$ (p mol · 10$^6$ cells$^{-1}$ · min$^{-1}$ · $\mu$M$^{-1}$) is the rate of diffusion and S ($\mu$M) is the concentration of either CPT-11 or SN-38. Values are mean ± SE. The major component of the uptake of CPT-11 lactone, SN-38 lactone and SN-38 carboxylate, respectively, was non-saturable and therefore, the K$_m$ and V$_{max}$ values were not determined (ND).

TABLE III

Effect of dinitrophenol, SN38-Glu and DNP-SG on initial uptake rate of CPT-11 and SN-38

| | CPT-11 carboxylate | | SN-38 carboxylate | | CPT-11 lactone | | SN-38 lactone | |
|---|---|---|---|---|---|---|---|---|
| | jejunum | ileum | jejunum | ileum | jejunum | ileum | jejunum | ileum |
| Dinitrophenol (1 mM) | | | | | | | | |
| Mean | 22.6 | 29.2 | 25.5 | 30.8 | 94.1 | 105.5 | 96.1 | 134.9 |
| (SE) | (13.5) | (9.2) | (12.4) | (13.1) | (18.4) | (15.6) | (14.7) | (19.0) |
| P value[1] (n = 5) | 0.016 | 0.008 | 0.008 | 0.016 | NS | NS | NS | NS |
| SN38-Glu (200 $\mu$M) | | | | | | | | |
| Mean | 108.9 | 93.9 | 40.1* | 28.9* | 88.9 | NE | 54.3 | NE |
| (SE) | (22.1) | (14.3) | (11.1) | (11.2) | (15.3) | | (20.6) | |
| DNP-SG (200 $\mu$M) | | | | | | | | |
| Mean | 103.2 | 105.8 | 32.0* | 28.5* | 105.4 | NE | 78.8 | NE |
| (SE) | (17.0) | (36.3) | (9.9) | (11.9) | (12.7) | | (24.4) | |
| p value[2] (n = 5) | NS | NS | 0.007 | 0.020 | NS | | NS | |

NE, not estimated; NS, not significantly different from control
NOTE: Dinitrophenol, SN-38 glucuronide (SN38-Glu) or 2,4-dinitrophenyl-S-glutathione (DNP-SG) was added to the indicated cell suspension before the addition of [$^{14}$C]CPT-11 (20 $\mu$M) and [$^{14}$C]SN-38 (2 $\mu$M), respectively (for details, see Materials and Methods). The initial uptake rate of CPT-11 and SN-38 in the presence of each compound was expressed as percentage (%) of control. Differences between dinitrophenol and its control were evaluated by [1]Mann-Whitney test. Differences among SN-38Glu, DNP-SG and their control were evaluated by [2]Kruskal-Wallis test, and the significant difference from respective control was analyzed according to Dunn's method (*p < 0.05).

Irinotecan Hydrochloride Formulations

In a preferred embodiment sodium bicarbonate, magnesium oxide and water are administered at more than a pH of about 7, preferably pH of 8 to 10 and most preferably a pH of 8 to 9, provided to patients treated with camptothecin compounds such as CPT-11 and its derivatives.

Further, the CPT-11 compounds of the present invention are useful in pharmaceutical compositions for systemic administration to humans and animals in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. For oral administration either solid or fluid unit dosage forms can be prepared with the compounds. The compounds are useful in pharmaceutical compositions (wt %) of the active ingredient with a carrier or vehicle in the composition in about 1 to 20% and preferably about 5 to 15%.

Either fluid or solid unit dosage forms can be readily prepared for oral administration. For example, the CPT-11 can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent which is inert and inserting this mixture into a hard gelatin capsule having the appropriate size. If soft capsules are desired a slurry of the compound with an acceptable vegetable, light petroleum, or other inert oil can be encapsulated by machine into a gelatin capsule.

Suspensions, syrups and elixirs may be used for oral administration of fluid unit dosage forms. A fluid preparation including oil may be used for oil soluble forms. A vegetable oil such as corn oil, peanut oil or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine or a biological sweetener and a flavoring agent in the form of an elixir.

Pharmaceutical compositions for parenteral and suppository administration can also be obtained using techniques standard in the art.

Suitable pharmaceutical carriers include-sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly (vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

The effective dosage for mammals may vary due to such factors as age, weight activity level or condition of the subject being treated. Typically, an effective dosage of a compound according to the present invention is about 10 mg/m$^2$ to 700 mg/m$^2$ when administered by either oral or rectal dose from 1 to 3 times daily. CPT-11 may preferably be administered once a week for a 1 to 5 week period. Administration times and dosages of CPT-11 for the treatment of cancers and tumors are known.

Administration of Irinotecan Hydrochloride

The mean terminal elimination half-life of irinotecan hydrochloride (Pharmacia-Upjohn) is about 6 hours.

Camptothecin compounds may also be administered alone or in combination with combination chemotherapy regimens including leucovorin, cisplatin, 5-FU, oxiplatin as well as other known chemotherapeutics. In an alternative embodiment camptothecin compounds such as irinotecan hydrochloride may also be administered with loperamide. camptothecin compounds such as irinotecan hydrochloride may also be administered with loperamide.

REFERENCES (1) Rivory L P, Robert J. Molecular, cellular, and clinical aspects of the pharmacology of 20(S)camptothecin and its derivatives. Pharmacol. Ther. 1995;68:269–96.
(2) Fukuoka M, Niitani H, Suzuki A, Motomiya M, Hasegawa K, Nishiwaki Y, et al. A phase II study of CPT-11, a new derivative of camptothecin, for previously untreated non-small-cell lung cancer. J. Clin. Oncol. 1992,10:16–20.
(3) Shimada Y, Yoshino M, Wakui A, Nakao I, Futatsuki K, Sakata Y, et al. Phase II study of CPT-11, a new camptothecin derivative, in metastatic colorectal cancer. J. Clin. Oncol. 1993; 11:909–913.
(4) McCloud E, Mathis R K, Grant K E, Said H M. Intestinal uptake of uridine in suckling rats: Mechanism and ontogeny. Proc Soc Exp Biol Med 1994;206:425–30.
(5) Masuda N, Fukuoka M, Kudoh S, Kusunoki Y, Matsui K, Takifuji N, et al. Phase I and pharmacologic study of irinotecan in combination with cisplatin for advanced lung cancer Br. J. Cancer 1993;68:777–782.
(6) Kudoh S, Fukuoka M, Masuda N, Kusunoki Y, Matsui K, Negoro S, et al. Relationship between CPT-11 pharmacokinetics and diarrhea in the combination chemotherapy of irinotecan (CPT-11) and cisplatin (CDDP). Proc. Am. Soc. Clin. Oncol. 1993;12–141.
(7) Gupta E, Lestingi T M, Mick R, Ramirez J, Vokes E E, Ratain M J. Metabolic fate of irinotecan in humans: correlation of glucuronidation with diarrhea. Cancer Res. 1994;54: 3723–3725.
(8) Sasaki Y, Ilakusui H, Mizuno S, Morita M, Miya T, Eguchi K, et al. A pharmacokinetic and pharmacodynamic analysis of CPT-I I and its active metabolite SN-38. Jpn. J. Cancer Res. 1995;86:101–110.
(9) Lokiec F, Canal P, Gay C, Chatelut E, Armand J P, Roche H, et al. Pharmacokinetics of irinotecan and its metabolites in human blood, bile, and urine. Cancer-Chemother-Pharmacol. 1995;36:79–82
(10) Kawato Y, Aonuma M, Hirota Y, Kuga H, Sato K. Intracellular roles of SN-38, a metabolite of the camptothecin derivative CPT-11, in the antitumor effect of CPT-11. Cancer Res. 1991;51:4187–91.
(11) Fassberg J, Stella V J. A kinetic and mechanistic study of the hydrolysis of camptothecin and some analogues. J. Pharm. Sci. 1992;81:676–684.
(12) Chu X Y, Kato Y, Sugiyama Y. Mutiplicity of biliary excretion mechanisms for irinotecan, CPT-11, and its metabolites in rats. Cancer Res. 1997;57:1934–38.
(13) Rivory L P, Bowles M R, Robert J. Pond S M. Conversion of irinotecan (CPT-11) to its active metabolite, 7-ethyl-10-hydroxycamptothecin (SN-38), by human liver carboxylesterase. Biochemical Pharmacol 1996;52:1103–11.
(14) Senter P D, Marquardt H, Thomas B A, Hammock B D, Frank I S, Svensson H P. The role of rat serum carboxylesterase in the activation of paclitaxel and camptothecin prodrugs. Cancer Research 1996;56:1471–4.
(15) Kaneda N, Yokokura T. Nonlinear pharmacokinetics of CPT-11 in rats. Cancer Res., 1990;50:1721–1725.
(16) Atsumi R, Suzuki W, Hakusui H. Identification of the metabolites of irinotecan. a new derivative of camptothecin, in rat bile and its biliary excretion. Xenobiotica, 1991;21:1159–1169.
(17) Chu X Y, Kato Y, Sugiyama Y. Multiplicity of biliary excretion mechanisms for irinotecan, CPT-11, and its metabolites in rats. Cancer Research, 1997;57:1934–38.
(18) Saxena M, Henderson G B. ATP-dependent efflux of 2,4-dinitrophenyl-S-glutathione. J. Biological Chemistry 1995;270:5312–19.
(19) Gore J, Hoinard C. Linoleic acid transport in hamster intestinal cells is carrier-mediated. J. Nutr. 1993, 123:66–73.
(20) Gore J, Hoinard C. Evidence of facilitated transport of Biotin by hamster enterocytes. J. Nutr. 1987;117:527–532.
(21) Shiau Y F, Levine G M. PH dependence of micellar diffusion and dissociation. Am. J. Physiol. 1980;239:G177–82.
(22) Chijiiwa K, Linscheer W G. Distribution and monomer activity of cholesterol in micellar bile salt: effect of cholesterol level. Am. J. Physiol. 1987;252:G309–314.
(23) Charman W N, Porter C J, Mithani S, Dressman J B. Physicochemical and physiological mechanisms for the effects of food on drug absorption: the role of lipids and pH. J Pharmacol Sci 1997;86:269–82.
(24) Sathirakul K, Suzuki H, Yasuda K, Hanano M, Tageya O, Horie T, et al. Kinetic analysis of hepatobiliary transport of organic anions in Eisai hyperbilirubinemic mutant rats. J. Pharmacol. Exp. Ther. 1993;265:1301–1312.
(25) Charman W N, Porter C J, Mithani S, Dressman J B. Physicochemical and physiological mechanisms for the effects of food on drug absorption: the role of lipids and pH. J Pharmacol Sci 1997;86:269–82.
(26) Kobayashi K, Bouscarel B, Matsuzaki Y, Ceryak S, Fromm H. Uptake mechanism of irinotecan (CPT-11) and its metabolite (SN-38) by hamster intestinal cells. Gastroenterology 1998; 114(4):A626 (proceeding).
(27) Ishikawa T, Muller M, Klunemann C, Schaub T, Keppler D. ATP-dependent primary active transport of cysteinyl leukotrienes across liver canalicular membrane. J. Biol. Chem. 1990;265:19279–19286.
(28) Nishida T. Hardenbrook C, Gatmaitan Z, Arias I. ATP-dependent organic anion transport system in normal and TR- rat liver canalicular membranes Am. J. Physiol. 1992:258:G629–G635.
(29) Pikuia S, Hayden J B, Awasthi S. Awasthi Y C, Zimniak P. Organic anion-transporting ATPase of rat liver. J. Biol. Chem. 1994;269:27566–27573.
(30) Burke T G, Mi Z. The structural basis of camptothecin interactions with human serum albumin: Impact on drug stability. J. Med. Chem. 1994;37:40–46.
(31) bile pH
(32) Slichenmyer W J, Rowinsky E K, Donehower R C, Kaufmann S H. The current status of camptothecin and analogues as antitumor agent. J. Natl. Cancer Inst. 1993;85:271–291.
(33) Atsumi R, Okazaki O, Hakusui H. Pharmacokinetics of SN-38 [(+)-(4S)-4,11-Diethyl-4,9-dihydroxy-1H-pyrano[3',4':6,7]-indolizino [1,2-b]quinoline-3,14(4H,12H)dione], an metabolite of irinotecan, after a single intravenous dosing of 14C-SN-38 to rats. Biol. Pharm. Bull. 1995;18:1114–1119.
(34) Araki E, Ishikawa M, Iigo M, Koide T, Itabashi M, Hoshi A. Relationship between development of diarrhea and the concentration of SN-38, an active metabolite of CPT-11, in the intestine and the blood plasma of athymic mice following intraperitoneal administration of CPT-11. Jpn. J. Cancer Res., 1991;51:4187–4191.
(35) Takasuna K, Hagiwara T, Hirohashi M, Kato M J, Nomura M, Nagai E, et al. Involvement of beta-glucuronidase in intestinal microflora in the intestinal toxicity of the antitumor camptothecin derivative irinotecan hydrochloride. Cancer Research. 1996;66:3752–3757.

(36) Abigerges D, Armand J P, Chabot G G, DaCosta L, Fadel E, Cote C, et al. Irinotecan (CPT-I I) high-dose escalation using intensive high-dose loperamide to control diarrhea. J. Natl. Cancer Inst., 1994;86:446–449.

(37) Kobayashi K, Shinbara A, Kamimura M, Takeda Y, Kudo K, Kabe J, at al. Irinotecan (CPT-11) in combination with weekly administration of cisplatin (CDDP for non-small-cell lung cancer. Cancer Chemother Pharmacol in printing.

(38) Bugaut M. Occurrence, absorption and metabolism of short chain fatty acids in the digestive track of mammals. Comp Biochem Physiol 1987;87B:439–72.

AKIMOTO K, KAWAI A, OHYA K. Kinetic studies of the hydrolysis and lactonization of camptothecin and its derivatives, CPT-11 and SN-38, in aqueous solution. Chem.Pharm.Bull., 42, 2135–2138 (1994).

ARAKI E, ISHIKAWA, M., IIGO, M., KOIDE. T., ITABASHI. M., HOSHI, A., Relationship between development of diarrhea and the concentration of SN-38, an active metabolite of CPT-11, in the intestine and the blood plasma of athymic mice following intraperitoneal administration of CPT-11. Jpn. J. Cancer Res., 84, 697–702 (1993).

ATSUMI, R., SUZUKI, W., HAKUSUI, H., Identification of the metabolites of irinotecan. a new derivative of camptothecin, in rat bile and its biliary excretion. Xenobiotica, 21, 1159–1169 (1991).

ATSUMI, R., OKAZAKI, O., HAKUSUI, H., Pharmacokinetics of SN-38 [(+)-(4S)-4,11-Diethyl-4,9-dihydroxy-1H-pyrano [3',4':6,7]-indolizino [1,2-b]quinoline-3,14 (4H,12H)-dione], an metabolite of irinotecan, after a single intravenous dosing of 14C-SN-38 to rats. Biol. Pharm. Bull., 18, 1114–1119 (1995).

BLEIBERG, H., CVITKOVIC, E., Characterisation and clinical management of CPT-11 (irinotecan)-induced adverse events: the European perspective. Eur. J. Cancer, 32A Suppl 3, S18–23 (1996).

BUGAUT, M., Occurrence, absorption and metabolism of short chain fatty acids in the digestive tract of mammals. Comp. Biochem. Physiol., 86B, 439–472 (1987).

BURKE, T. G., MI, Z., The structural basis of camptothecin interactions with human serum albumin: Impact on drug stability. J. Med. Chem.,37, 40–46 (1994).

CHARMAN, W. N., PORTER, C. J., MITHANI, S., DRESSMAN, J. B., Physiochemical and physiological mechanisms for the effects of food on drug absorption: the role of lipids and pH. J.Pharm.Sci., 86, 269–282 (1997).

CHU, X. Y., KATO, Y., NIINUMA, K., SUDO, K., HAKUSUI, H., SUGIYAMA, Y., Multispecific organic anion transporter is responsible for the biliary excretion of the camptothecin derivative irinotecan and its metabolites in rats. J. Pharmacol. Exp. Ther., 281, 304–314 (1997a).

CHU, X. Y., KATO, Y., SUGIYAMA, Y., Multiplicity of biliary excretion mechanisms for irinotecan, CPT-11, and its metabolites in rats. Cancer Research, 57, 1934–1938 (1997b).

CUNNINGHAM, D., PYRHÖNEN, S., JAMES, R. D., PUNT, C. J. A., HICKISH, T. S., HEIKKILA, R., JOHANNESES, T., STARKHAMMAR, H., TOPHAM, C. A., ONG, E., HERAIT, P., JACQUES, C., A phase III multicenter randomized study of CPT-11 versus supportive care alone in patients with 5-FU-resistant metastatic colorectal cancer. Proc. Am. Soc. Clin. Oncol., 17, 1a (1998).

FASSBERG, J., STELLA, V. J., A kinetic and mechanistic study of the hydrolysis of camptothecin and some analogues. J. Pharm. Sci., 81, 676–684 (1992).

FUKUOKA, M., NIITANI, H., SUZUKI, A., MOTOMIYA, M., HASEGAWA, K., NISHIWAKI, Y., KURIYAMA, T., ARIYOSHI, Y., NEGORO, S., MATSUDA, N., NAKAJIMA, S., TAGUCHI, T., for the CPT-11 Lung Cancer Study Group. A phase II study of CPT-11, a new derivative of camptothecin, for previously untreated non-small-cell lung cancer. J. Clin. Oncol., 10, 16–20 (1992).

GORE, J., HOINARD, C., Linoleic acid transport in hamster intestinal cells is carrier-mediated. J. Nutr., 123, 66–73 (1993).

HAAZ, M. C., RIVORY, L. P., RISHE, C., ROBERT, J. Metabolism of irinotecan (CPT-11) by human hepatic microsomes: participation of cytochrome P-450 3A (CYP3A) and drug interactions. Proc. Am. Assoc. Cancer Res., 38, 17 (1997) (Abstr.).

IKUNO, N., SODA, H., WATANABE, M., OKA, M., Irinotecan (CPT-11) and characteristic mucosal change in the mouse ileum and cecum. J. Natl. Cancer Inst., 87, 1876–1883 (1995).

KAWATO, Y., AONUMA, M., HIROTA, Y., KUGA, H., SATO, K., Intracellular roles of SN-38, a metabolite of the camptothecin derivative CPT-11, in the antitumor effect of CPT-11. Cancer Res., 51, 4187–4191 (1991).

KOBAYASHI, K., BOUSCAREL, B., MATSUZAKI, Y., CERYAK, S., FROMM, H., Uptake mechanism of irinotecan (CPT-11) and its metabolite (SN-38) by hamster intestinal cells. Gastroenterology,114(4), A626, proceeding (1998a).

KOBAYASHI, K., SHINBARA, A., KAMIMURA, M., TAKEDA, Y., KUDO, K., KABE, J., HIBINO, S., HINO, M., SHIBUYA, M., KUDOH, S., Irinotecan (CPT-11) in combination with weekly administration of cisplatin (CDDP) for non-small-cell lung cancer. Cancer Chemother. Pharmacol., 42, 53–58 (1998b).

LOKIEC, F., CANAL, P., GAY, C., CHATELUT, E., ARMAND, J. P., ROCHE, H., BUGAT, R., GONCALVES, E., MATHIEU-BOUE, A., Pharmacokinetics of irinotecan and its metabolites in human blood, bile, and urine. Cancer Chemother. Pharmacol., 36, 79–82 (1995).

MCCLOUD, E., MATHIS, R. K., GRANT, K. E., SAID, H. M., Intestinal uptake of uridine in suckling rats: mechanism and ontogeny. Proc. Soc. Exp. Biol. Med., 206, 425–430 (1994).

MOSMANN, T., Rapid colorimetiric assay for cellular growth and survival: Application to proliferation and cytotoxicity assay. J. Immunol. Methods, 65, 55–63 (1983).

RIVORY, L. P., BOWLES, M. R., ROBERT, J., POND, S. M., Conversion of irinotecan (CPT-11) to its active metabolite, 7-ethyl-10-hydroxycamptothecin (SN-38), by human liver carboxylesterase. Biochemical Pharmacol., 52, 1103–1111 (1996a).

RIVORY, L. P., RIOU, J. F., HAAZ, M. C., SABLE, S., VUIHORGNE, M., COMERSON, A., POND, S. M., ROBERT, J. Identification and properties of a major plasma metabolite of irinotecan (CPT-11) isolated from the plasma of patients. Cancer Res., 56, 3689–3694 (1996b).

TAKATSUNA, K., HAGIWARA, T., HIROHASHI, M., KATO, M., NOMURA, M., NAGAI, E., YOKOI, T., KAMATAKI, T., Involvement of beta-glucuronidase in intestinal microflora in the intestinal toxicity of the antitumor camptothecin derivative irinotecan hydrochloride. Cancer Research, 56, 3752–3757 (1996).

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

What is claimed is:

1. A method of inhibiting a diarrhea side effect in a patient receiving a treatment with a camptothecin compound, the method comprising:

administering a camptothecin compound selected from the group consisting of irinotecan hydrochloride CPT-11-Glu, SN-38-Glu, SN-38, 10,11-methylenedioxy-20(RS)-camptothecin, 9-amino-20(RS)-camptothecin and 7-hydroxy-methyl camptothecin in the amount of 10 $mg/m^2$ to 700 $mg/m^2$ to a patient in need thereof while maintaining the intestinal lumen of the patient at an alkaline pH of 7 to 10 by administering ursodeoxycholic acid to the patient to stimulate bicarbonate secretion into bile of the patient.

* * * * *